(12) United States Patent
Kawashima et al.

(10) Patent No.: US 9,415,412 B2
(45) Date of Patent: Aug. 16, 2016

(54) ATOMIZER

(71) Applicant: Sumitomo Chemical Company, Limited, Tokyo (JP)

(72) Inventors: Shinsuke Kawashima, Takarazuka (JP); Daisuke Takahata, Saitama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 140 days.

(21) Appl. No.: 14/388,451

(22) PCT Filed: Mar. 25, 2013

(86) PCT No.: PCT/JP2013/058503
§ 371 (c)(1),
(2) Date: Sep. 26, 2014

(87) PCT Pub. No.: WO2013/146639
PCT Pub. Date: Oct. 3, 2013

(65) Prior Publication Data
US 2015/0054182 A1  Feb. 26, 2015

(30) Foreign Application Priority Data

Mar. 30, 2012  (JP) .................................. 2012-080984

(51) Int. Cl.
*B05B 17/06* (2006.01)
*B01F 3/04* (2006.01)
(Continued)

(52) U.S. Cl.
CPC ................ *B05B 17/06* (2013.01); *A01M 1/205* (2013.01); *A01M 29/12* (2013.01); *A61L 9/14* (2013.01);
(Continued)

(58) Field of Classification Search
CPC ...... B01F 3/04; B01F 3/04021; B01F 3/0407; B01F 3/04007; B01F 3/04085; B05B 17/06; B05B 17/0607; B05B 17/0638; B05B 17/0646

USPC ................ 261/72.1, 78.2, 104, 107, DIG. 65, 261/DIG. 88; 239/102.1, 102.2
See application file for complete search history.

(56) References Cited

U.S. PATENT DOCUMENTS 7,424,979 B1 * 9/2008 Chen ................... B05B 17/0684
239/102.1
8,296,993 B2  10/2012 Modlin et al.
(Continued)

FOREIGN PATENT DOCUMENTS

EP  1382399 A1  1/2004
EP  1773413 B1  10/2007
(Continued)

OTHER PUBLICATIONS

Extended Search Report issued Jul. 10, 2015 in EP Application No. 12862169.5.
(Continued)

*Primary Examiner* — Robert A Hopkins
(74) *Attorney, Agent, or Firm* — Panitch Schwarze Belisario & Nadel LLP (57) ABSTRACT

An atomizer is provided to include a pivot member mounted on an upper portion of a device body so as to pivot up and down. The pivot member includes a holding portion configured to hold a vibrating plate movable up and down relative to the pivot member so as to bring the vibrating plate into face contact with the upper end surface of a wick by its own weight when the pivot member pivots downward. The device body includes a restriction portion that comes into contact with the pivot member to restrict the pivoting downward of the pivot member, while the vibrating plate is in face contact with the upper end surface of the wick.

2 Claims, 6 Drawing Sheets

(51) Int. Cl.
*B05B 15/06* (2006.01)
*B05B 17/00* (2006.01)
*A01M 29/12* (2011.01)
*A01M 1/20* (2006.01)
*A61L 9/14* (2006.01)
*F24F 6/12* (2006.01)

(52) U.S. Cl.
CPC .......... *B01F 3/0407* (2013.01); *B01F 3/04085* (2013.01); *B05B 15/06* (2013.01); *B05B 17/0607* (2013.01); *B05B 17/0646* (2013.01); *B05B 17/0684* (2013.01); *A61L 2209/132* (2013.01); *A61L 2209/135* (2013.01); *F24F 6/12* (2013.01)

(56) References Cited

U.S. PATENT DOCUMENTS

| | | | |
|---|---|---|---|
| 2006/0011737 A1* | 1/2006 | Amenos | A01M 1/2033 239/102.1 |
| 2007/0237498 A1 | 10/2007 | Helf et al. | |
| 2008/0006264 A1 | 1/2008 | Gallem et al. | |
| 2008/0011875 A1 | 1/2008 | Sipinski et al. | |
| 2008/0073447 A1 | 3/2008 | Wang et al. | |
| 2008/0308096 A1 | 12/2008 | Borgschulte et al. | |
| 2009/0224064 A1 | 9/2009 | Brodbeck et al. | |
| 2012/0111970 A1 | 5/2012 | Hogan et al. | |

FOREIGN PATENT DOCUMENTS

| | | |
|---|---|---|
| EP | 2100670 A1 | 9/2009 |
| JP | H06-320083 A | 11/1994 |
| JP | 2008-188515 A | 8/2008 |
| JP | 2009-118792 A | 6/2009 |
| JP | 2011-075196 A | 4/2011 |
| JP | 2011-130742 A | 7/2011 |
| JP | 2012-011319 A | 1/2012 |
| WO | 2010134164 A1 | 11/2010 |

OTHER PUBLICATIONS

Office Action issued May 7, 2015 in U.S. Appl. No. 14/366,430 by Kawano.
Office Action issued Dec. 19, 2014 in U.S. Appl. No. 13/883,840.
Int'l Search Report issued Jun. 25, 2013 in Int'l Application No. PCT/JP2013/058503.
Search Report issued Oct. 28, 2015 in EP Application No. 13769785.0.

* cited by examiner

ATOMIZER

CROSS-REFERENCE TO RELATED APPLICATION

This application is a Section 371 of International Application No. PCT/JP2013/058503, filed Mar. 25, 2013, which was published in the Japanese language on Oct. 3, 2013, under International Publication No. WO 2013/146639 A1, and the disclosure of which is incorporated herein by reference.

TECHNICAL FIELD

The present invention relates to an atomizer which atomizes a liquid such as water, a chemical liquid, or the like.

BACKGROUND ART

Conventionally, an atomizer described in Patent Literature 1 has been known as an atomizer which atomizes a liquid such as water, a chemical liquid, or the like through a large number of pores formed in a vibrating plate by vibrating the vibrating plate while keeping the vibrating plate in face contact with an upper end surface of a wick that has absorbed the liquid. In the atomizer, while a lower end portion of the wick (liquid absorbing material) is sunk in a liquid within a liquid reserve chamber, an upper end portion of the wick is brought into face contact with the vibrating plate by the urging force of a spring, and the liquid absorbed from the lower end portion of the wick is supplied from the surface of the upper end portion of the wick to the vibration plate.

However, in the atomizer described in Patent Literature 1, the urging force of the spring is applied to one point away from the center of the wick, and thus it is practically difficult to adjust the pressing force between the vibrating plate and the wick into an appropriate state. Thus, in this situation, it is difficult for the atomizer to keep the vibrating plate and the wick in a stable contact state, and improvement thereof is desired.

Therefore, as shown in Patent Literature 2, an atomizer is proposed in which a vibrating plate is supported by a guide member mounted on an upper portion of a liquid reservoir so that the vibrating plate may be movable up and down, and the vibrating plate and a wick are brought into face contact with each other by the weight of the vibrating plate.

CITATION LIST

Patent Literature

PATENT LITERATURE 1: Japanese Laid-Open Patent Publication No. 6-320083
PATENT LITERATURE 2: Japanese Laid-Open Patent Publication No. 2008-188515

SUMMARY OF INVENTION

Technical Problem

However, in the atomizer described in Patent Literature 2, in refilling the liquid reservoir with a liquid, the guide member has to be detached and separated from the liquid reservoir. Thus, after the refilling with the liquid, in mounting the liquid reservoir on the guide member again, due to the guide member being tilted relative to the liquid reservoir, the guide member may not be set at an appropriate position. In this case, a contact state of the vibrating plate and the wick is not stabilized, and thus there is the problem that the efficiency of atomizing the liquid is decreased.

The present invention has been made in view of such a circumstance, and an object of the present invention is to provide an atomizer which allows a vibrating plate and a wick to be kept in a stable contact state even after an operation of refilling with a liquid.

Solution to Problem

An atomizer of the present invention comprises:
a device body;
a liquid reservoir provided within the device body and configured to reserve a liquid therein;
a wick that is to be sunk at its lower end portion in a liquid reserved within the liquid reservoir;
a vibrating plate having a large number of pores and being configured to come into face contact with an upper end surface of the wick, the atomizer being configured to atomize through the pores of the vibrating plate a liquid absorbed up to the upper end surface of the wick, by vibrating the vibrating plate while keeping the vibrating plate in face contact with the upper end surface of the wick; wherein
the atomizer further comprises a pivot member mounted on an upper portion of the device body so as to pivot up and down,
the pivot member has a holding portion to hold the vibrating plate movable up and down relative to the pivot member so as to bring the vibrating plate into face contact with the upper end surface of the wick by the own weight of the vibrating plate when the pivot member pivots downward, and
the device body has a restriction portion that comes into contact with the pivot member to restrict the pivoting downward of the pivot member while the vibrating plate is in face contact with the upper end surface of the wick.

According to the present invention, since the pivot member which holds the vibrating plate is mounted on the upper portion of the device body so as to pivot up and down, the pivot member pivots upward together with the vibrating plate and it is possible to refill the liquid reservoir with the liquid. Then, after the refilling with the liquid, the pivot member pivots downward together with the vibrating plate so as to be brought into contact with the restriction portion of the device body, thereby the vibrating plate can be brought into face contact with the upper end surface of the wick by own weight of the vibrating plate. Accordingly, even after the operation of refilling with the liquid, it is possible to keep the vibrating plate and the wick in a stable contact state.

In addition, preferably, the device body has a recessed accommodation portion capable of accommodating a battery that is a driving source to vibrate the vibrating plate, and the pivot member has a cover portion to overlie at least a part of the battery accommodated in the accommodation portion when the pivot member pivots downward.

In this case, it is possible to use the pivot member also as a cover member which overlies the battery accommodated in the accommodation portion of the device body, and thus it is possible to simplify the configuration of the atomizer.

Advantageous Effects of Invention

According to the atomizer of the present invention, it is possible to keep the vibrating plate and the wick in a stable contact state even after an operation of refilling with the liquid.

DESCRIPTION OF EMBODIMENTS

Hereafter, an embodiment of the present invention will be described with reference to the drawings.

Figure 1:
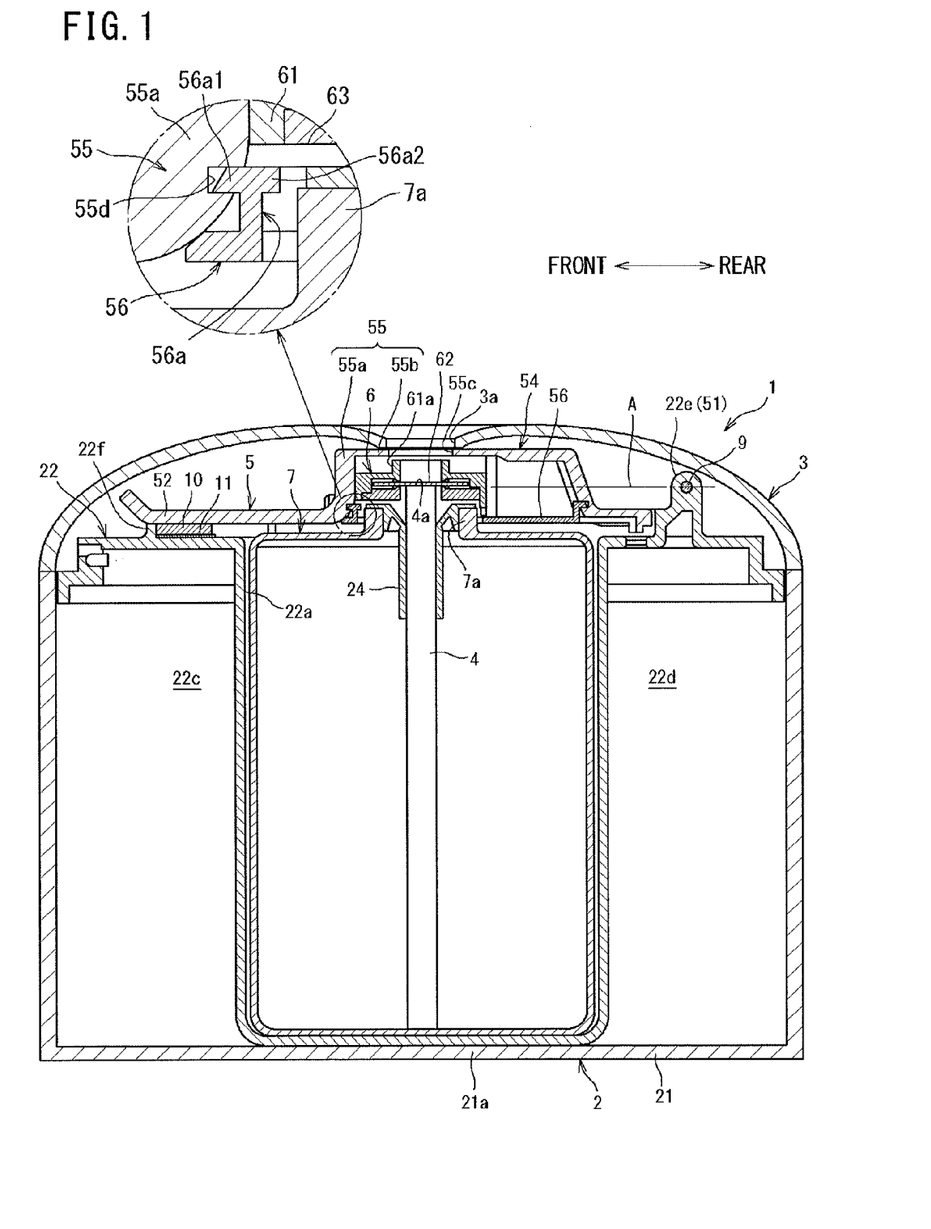
FIG. 1 is a cross-sectional side view showing an atomizer according to an embodiment of the present invention.

FIG. 1 is a cross-sectional side view showing an atomizer according to an embodiment of the present invention. In FIG. 1, the atomizer 1 atomizes, for example, a chemical liquid for avoiding insect pests (a liquid). The atomizer 1 includes a device body 2, a lid 3 which covers an upper portion of the device body 2, a liquid reservoir 7 which is provided in the device body 2 and reserves the chemical liquid, a wick 4 which is held by the liquid reservoir 7, a pivot member 5 which is mounted on the upper portion of the device body 2 so as to pivot up and down, and a vibration unit 6 which is held by the pivot member 5. An opening 3a is formed in a center portion of the lid 3 so as to extend therethrough in a thickness direction of the lid.

Figure 2:
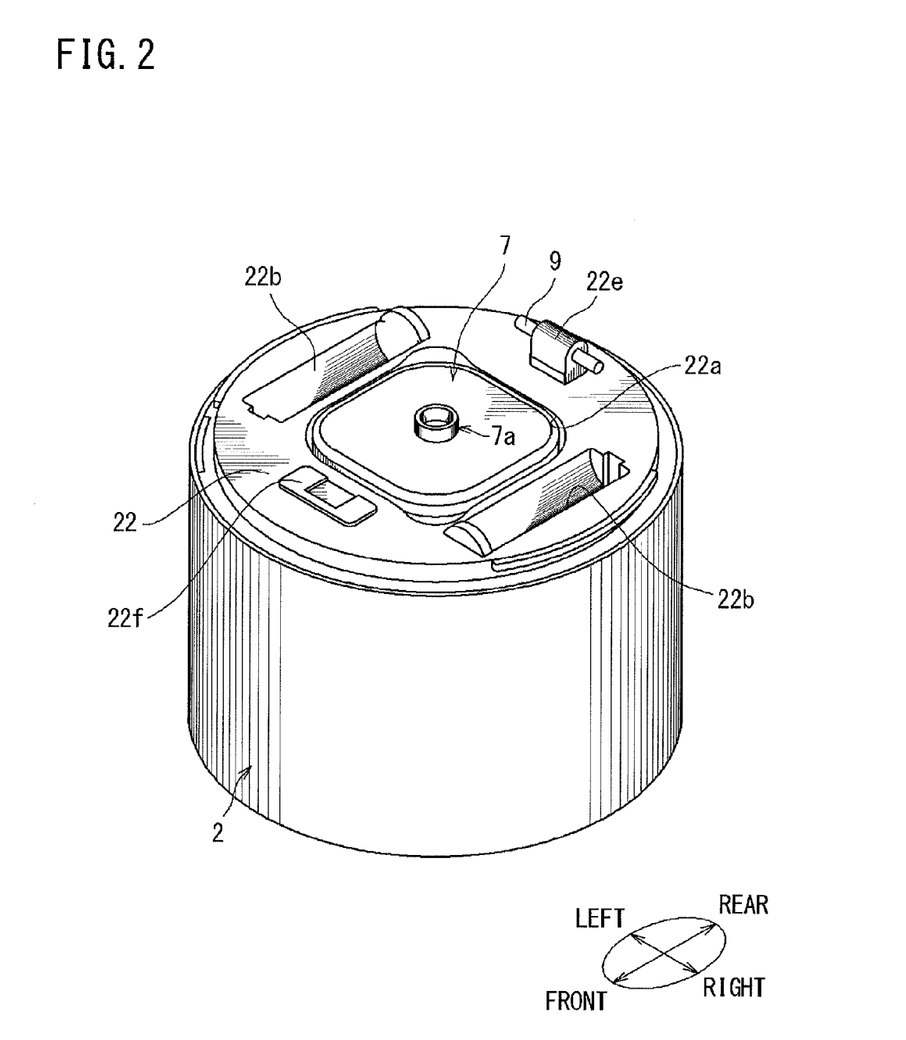
FIG. 2 is a perspective view showing a device body.

FIG. 2 is a perspective view showing the device body 2. In FIGS. 1 and 2, the device body 2 is formed such that the outer shape thereof is a cylindrical shape with a bottom, and includes a partition portion 22 which forms a plurality of accommodation portions 22a to 22d within the device body 2. At a bottom portion of the device body 2, a horizontal portion 21 is formed such that the device body 2 can be placed at a prescribed location in a stable state. The liquid reservoir 7 includes a cylindrical opening portion 7a which projects upward at the center of an upper portion thereof, and a wick holder 24 which holds the wick 4 in a state where the wick 4 is inserted in the liquid reservoir 7 is fitted to the opening portion 7a.

The partition portion 22 is composed of a plate member having concave portions and convex portions. As shown in FIG. 2, the partition portion 22 includes the first accommodation portion 22a formed in a recess shape and a pair of the second accommodation portions 22b formed in a recess shape at both right and left sides of the first accommodation portion 22a. The liquid reservoir 7 is detachably accommodated in the first accommodation portion 22a. Two AA size batteries B which are driving sources which drive a later-described vibrating plate 62 are accommodated in the second accommodation portions 22b, respectively (see FIG. 3).

As shown in FIG. 1, the third accommodation portion 22c and the fourth accommodation portion 22d which accommodate control boards (not shown) which control driving of the batteries B, etc. are formed between the undersurface of the partition portion 22 and the bottom portion of the device body 2 at both front and rear sides of the first accommodation portion 22a. A bracket portion 22e which supports the pivot member 5 such that the pivot member 5 may be movable pivotally upward is integrally formed at a rear portion of the first accommodation portion 22a of the partition portion 22. In addition, a restriction portion 22f which projects upward is integrally formed at the front portion of the first accommodation portion 22a of the partition portion 22 (also see FIG. 2). The restriction portion 22f restricts downward pivot of the pivot member 5 by bringing a contact portion 52 (described later) of the pivot member 5 into contact with the restriction portion 22f.

In FIG. 1, the wick 4 absorbs the chemical liquid within the liquid reservoir 7 by a capillary phenomenon, and, for example, is formed in a columnar shape of a synthetic resin material including polypropylene (PP) and polyethylene (PE). The wick 4 is held at a center portion thereof by the wick holder 24 in a state where a lower end portion thereof is sunk in the chemical liquid within the liquid reservoir 7 and an upper end portion thereof projects above the opening portion 7a of the liquid reservoir 7. Thus, an upper end surface 4a of the wick 4 is kept in a horizontal state at all times.

Figure 3:
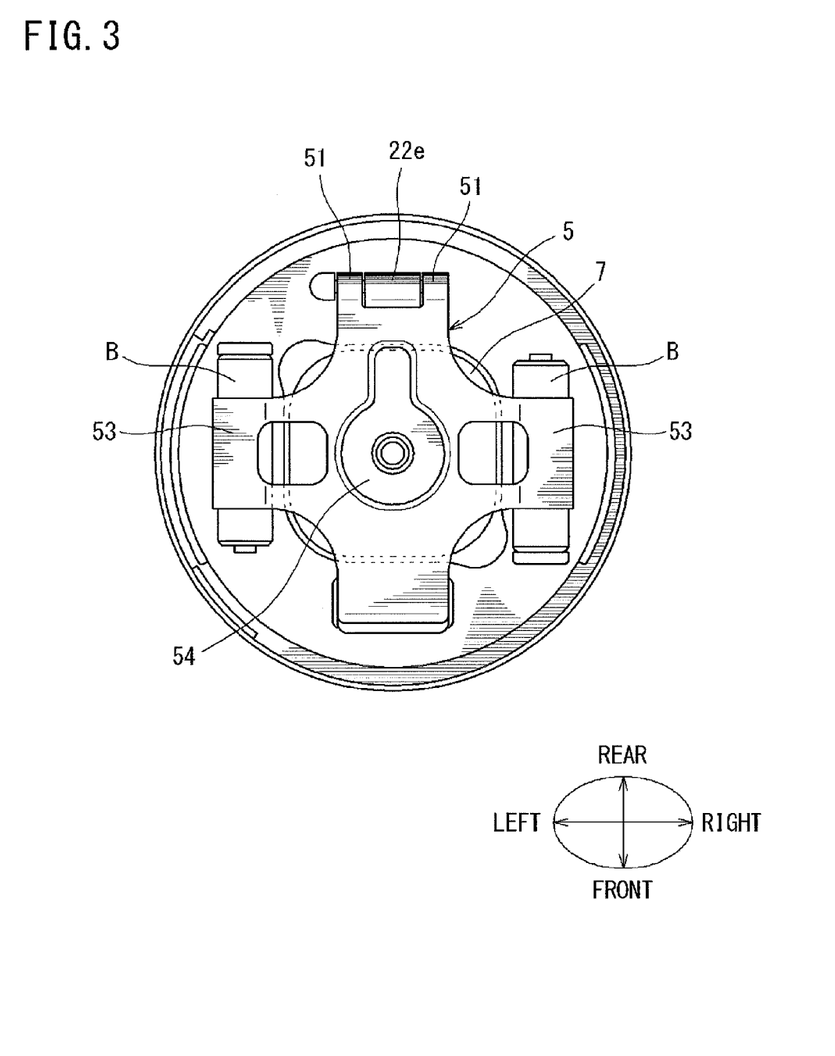
FIG. 3 is a plan view of the atomizer, showing a state where a lid has been detached therefrom.
Figure 4:
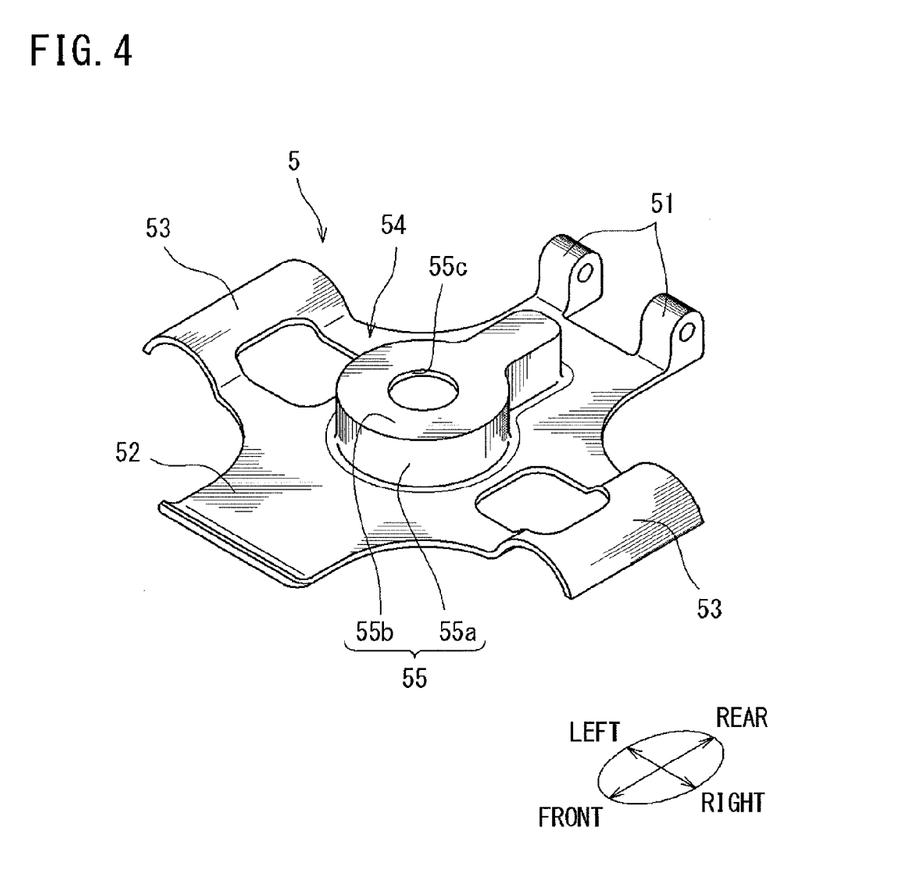
FIG. 4 is a perspective view showing a pivot member.

FIG. 3 is a plan view of the atomizer 1, showing a state where the lid 3 has been detached therefrom. FIG. 4 is a perspective view showing the pivot member 5. In FIGS. 3 and 4, the pivot member 5 is composed of a plate member having concave portions and convex portions, and includes a pair of hinge portions 51 which are integrally provided at a rear portion thereof so as to project therefrom, the contact portion 52 which is integrally formed at a front portion thereof, a pair of cover portions 53 which are integrally formed at both right and left sides, and a holding portion 54 which is provided at a center portion thereof.

Figure 5:
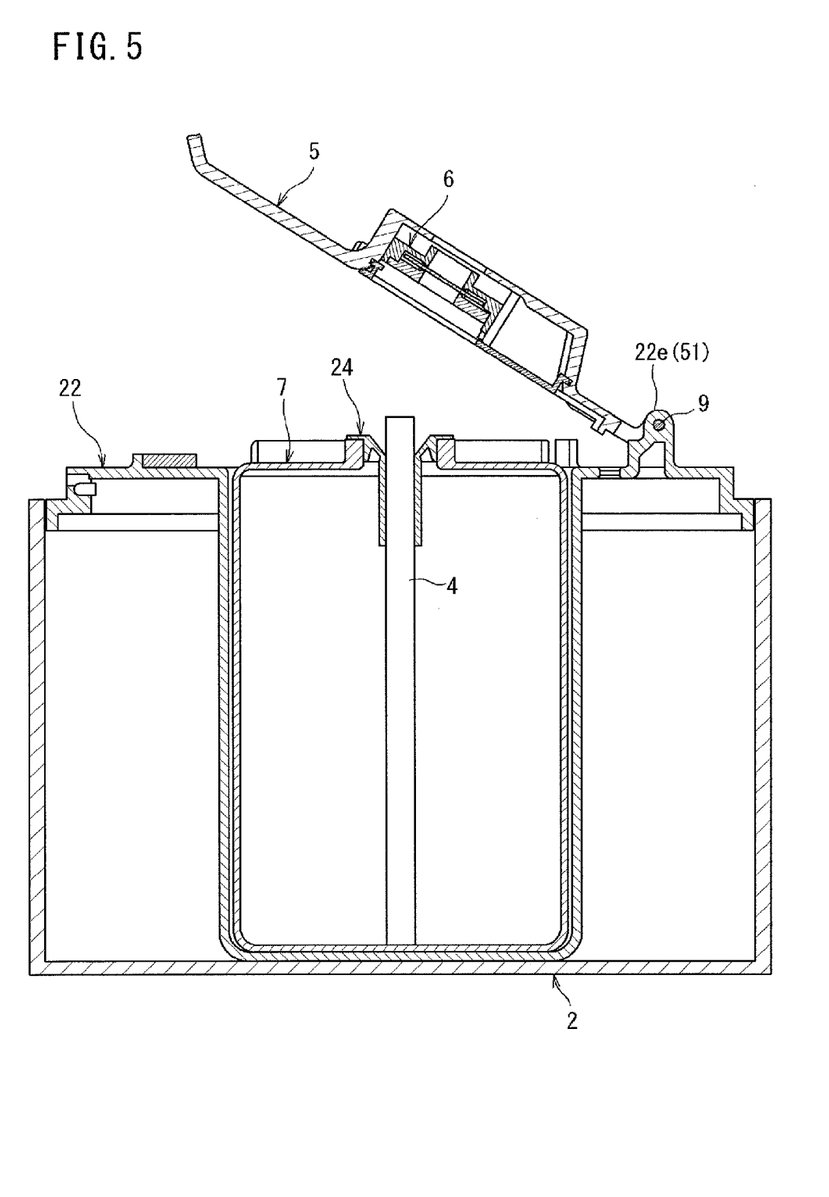
FIG. 5 is a cross-sectional side view of the atomizer, showing a state where the pivot member has been pivoted upward.

The outer shape of the hinge portions 51 is the same as the shape of the bracket portion 22e (see FIG. 1) of the partition portion 22. As shown in FIG. 4, the hinge portions 51 are pivotally supported by the bracket portion 22e via a support pin 9 (see FIG. 2) in a state where the hinge portions 51 are disposed closely at both right and left sides of the bracket portion 22e. Thus, as shown in FIG. 5, the pivot member 5 can pivot upward relative to the device body 2 from a state where the pivot member 5 has pivoted downward as shown in FIG. 1.

As shown in FIG. 1, pivoting downward of the pivot member 5 brings the vibrating plate 62 into face contact with the upper end surface 4a of the wick 4, and the contact portion 52 is configured so as to be brought into contact with the restriction portion 22f of the partition portion 22 while keeping the position. A permanent magnet 10 is fixed to the lower surface of the contact portion 52. When the contact portion 52 is brought into contact with the restriction portion 22f, the permanent magnet 10 attracts a metal plate 11 fixed to the restriction portion 22f, by a magnetic force thereof. Thus, it is possible to hold the pivot member 5 in a state where the pivot member 5 has pivoted downward.

As shown in FIG. 4, the lower surface of each cover portion 53 is formed in a concave arc shape over the entire length thereof in a front-rear direction. Thus, as shown in FIG. 3, the cover portions 53 overlies longitudinal center portions of the batteries B accommodated in the second accommodation portions 22b of the partition portion 22, in a state where the pivot member 5 has pivoted downward. It should be noted that as shown in FIG. 3, the center portion of the pivot member 5 also serves as a cover member which overlies the liquid reservoir 7.

In FIGS. 1 and 4, the holding portion 54 holds the vibration unit 6 so that the vibration unit 6 may be movable up and down relative to the pivot member 5. The holding portion 54 of the present embodiment includes: a holding portion body 55 which is integrally formed at the center portion of the pivot member 5 so as to project upward therefrom; and an engagement portion 56 which is disengageably engaged with the holding portion body 55.

The holding portion body 55 includes a cylindrical portion 55a and a disc portion 55b which is integrally formed at an upper end of the cylindrical portion 55a, and an opening 55c is formed in a center portion of the disc portion 55b so as to be substantially concentric with the opening 3a of the lid 3. A prescribed gap S is formed in the cylindrical portion 55a in an updown direction and a support member 61 (described later) of the vibration unit 6 is disposed in the gap S so as to be movable up and down. The gap S is set with such a size as to allow the vibration unit 6 to be moved up and down by ±1 mm.

In FIG. 1, the engagement portion 56 of the holding portion 54 is composed of a plate member formed in an annular shape, and the opening portion 7a of the liquid reservoir 7 is inserted in the inner periphery of the engagement portion 56 in a state where the pivot member 5 has been pivoted downward. As shown in an enlarged view of an alternate long and short dash line portion of FIG. 1, stoppers 56a each having a T cross-sectional shape are formed on the inner peripheral side of the upper surface of the engagement portion 56 and at a plurality of locations in a circumferential direction so as to project therefrom. Each stopper 56a includes a claw portion 56a1 which is detachably engaged with an engagement groove 55d formed on the inner peripheral surface of the cylindrical portion 55a of the holding portion body 55. Thus, the engagement portion 56 is detachably engaged with the holding portion body 55. In addition, each stopper 56a includes a contact portion 56a2 which is brought into contact with the lower surface of the support member 61 when the vibration unit 6 is moved downward. Thus, it is possible to restrain the vibration unit 6 accommodated in the holding portion body 55, from falling off from the holding portion body 55.

In FIG. 1, the vibration unit 6 includes: the support member 61 which is disposed within the cylindrical portion 55a of the holding portion 54; the vibrating plate 62 which is disposed within the support member 61; and a fixing member 63 which is disengageably engaged with a lower portion of the support member 61.

Figure 6:
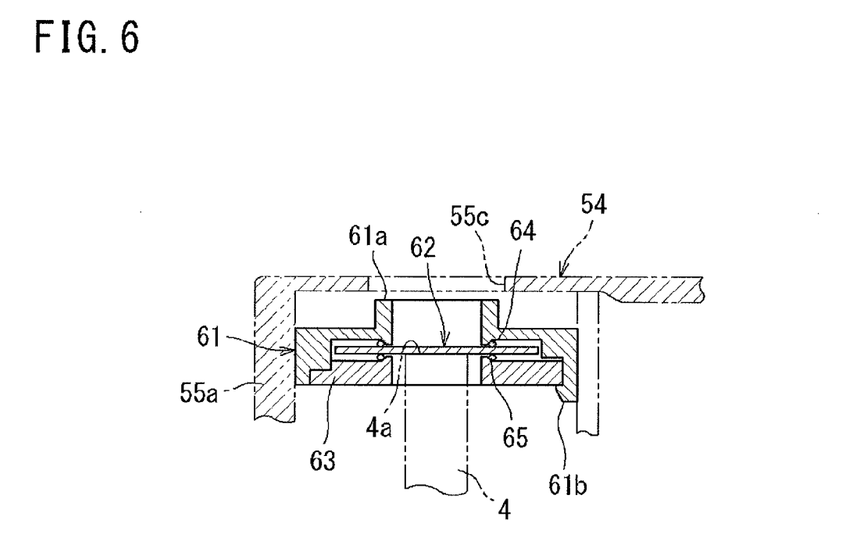
FIG. 6 is a cross-sectional side view showing a vibration unit.

FIG. 6 is a cross-sectional side view showing the vibration unit 6. In FIG. 6, the support member 61 is formed in a cylindrical shape, and is disposed within the cylindrical portion 55a of the holding portion 54 so as to be movable up and down. A cylindrical opening portion 61a is formed at a center portion of the support member 61 so as to project upward therefrom. The outer diameter of the opening portion 61a is set so as to be smaller than the diameter of the opening 55c of the holding portion 54, such that when the support member 61 is moved upward, the opening portion 61a is inserted into the opening 55c.

The vibrating plate 62 is formed in a disc shape, and a large number of pores (not shown) are formed in a center portion thereof so as to extend therethrough in a thickness direction thereof. The vibrating plate 62 is disposed within the support member 61 via an O-ring 64 which is an elastic member. A thin-plate-shaped piezoelectric ceramic (not shown) formed of an ultrasonic piezoelectric material is adhered to the upper surface of the vibrating plate 62. By applying a drive voltage to the piezoelectric ceramic, the vibrating plate 62 is vibrated with the piezoelectric ceramic.

The fixing member 63 is composed of an annular plate, and is disposed within the support member 61 and below the vibrating plate 62 via an O-ring 65 which is an elastic member. A plurality of claw portions 61b which are provided at the outer periphery of the lower end of the support member 61 so as to project therefrom are engaged with the lower surface of the fixing member 63. Thus, the vibrating plate 62 is held between the support member 61 and the fixing member 63 via the O-rings 64 and 65 in a horizontal state. The inner diameter of the fixing member 63 is set so as to be larger than the outer diameter of the wick 4, such that the upper end portion of the wick 4 is allowed to be inserted into the fixing member 63.

With the configuration described above, by taking out the wick 4 from the opening portion 7a of the liquid reservoir 7 in a state where the pivot member 5 has been pivoted upward together with the vibration unit 6 as shown in FIG. 5, it is possible to refill the liquid reservoir 7 with the chemical liquid through the opening portion 7a. It should be noted that since the liquid reservoir 7 of the present embodiment is detachably accommodated in the first accommodation portion 22a, the liquid reservoir 7 accommodated in the first accommodation portion 22a may be taken out and replaced with a new liquid reservoir 7 filled with the chemical liquid.

After the liquid reservoir 7 is refilled with the chemical liquid, as shown in FIG. 1, the pivot member 5 is pivoted downward together with the vibration unit 6 to bring the contact portion 52 of the pivot member 5 into contact with the restriction portion 22f of the device body 2, whereby the entire vibration unit 6 moves downward by the own weight of the vibration unit and the lower surface of the vibrating plate 62 can be brought into face contact with the upper end surface 4a of the wick 4. At that time, the lower surface of the vibrating plate 62 is located so as to be flush with a horizontal plane A including a pivot fulcrum of the pivot member 5 (the axis of the support pin 9). In this state, when the vibrating plate 62 is vibrated, it is possible to atomize the chemical liquid that has been absorbed up to the upper end surface 4a of the wick 4, upward through the pores of the vibrating plate 62. The upward atomized chemical liquid is discharged through the opening portion 61a of the support member 61, the opening 55c of the holding portion 54, and the opening 3a of the lid 3 to the outside.

As described above, according to the atomizer 1 of the present invention, since the pivot member 5 which holds the vibrating plate 62 is mounted on the upper portion of the device body 2 so as to pivot up and down, and the pivot member 5 pivots upward together with the vibrating plate 62, it is possible to refill the liquid reservoir 7 with the chemical liquid. After the refilling with the chemical liquid, the pivot member 5 pivots downward together with the vibrating plate 62 to be brought into contact with the restriction portion 22f of the device body 2, whereby the vibrating plate 62 can be brought into face contact with the upper end surface 4a of the wick 4 by the own weight thereof. Therefore, even after the operation of refilling with the chemical liquid, it is possible to keep the vibrating plate 62 and the wick 4 in a stable contact state.

In addition, since the pivot member 5 includes the cover portions 53 which overlie a part (the longitudinal center portions) of the batteries B accommodated in the second accommodation portions 22b of the partition portion 22 by pivoting the pivot member 5 downward, it is possible to use the pivot member 5 also as a cover member which overlies the batteries B. Thus, it is possible to simplify the configuration of the atomizer 1.

It should be noted that the present invention is not limited to the above-described embodiment and may be implemented by appropriately changing the embodiment. For example, the liquid reservoir 7 in the present embodiment is detachably mounted in the device body 2, but may be fixed to the device body 2.

The cover portions 53 of the pivot member 5 in the present embodiment overlie the parts of the batteries B, but may overlie the entire batteries B.

Furthermore, in the above-described embodiment, the example has been described in which the vibrating plate 62 is brought into face contact with the upper end surface 4a of the wick 4 by the own weight thereof. However, for example, a disc spring may be provided above the support member 61 so that the center thereof substantially may coincide with the center of the cylindrical support member 61, and the vibrating plate 62 may be brought into face contact with the upper end surface 4a of the wick 4 by the urging force of the disc spring. Or, a coil spring whose center substantially coincides with the center of the support member 61 may be used instead of the disc spring.

The restriction portion 22f in the present embodiment is formed so as to be integrated with the partition portion 22, but may be formed so as to be integrated with the device body 2 other than the partition portion 22. The restriction portion 22_f_ may be provided as a member separate from the device body 2.

The atomizer 1 of the present invention is not limited to the case of atomizing the chemical liquid for avoiding insect pests, and is also applicable to other uses such as the case of atomizing water for humidification.

REFERENCE SIGNS LIST

1 atomizer
2 device body
4 wick
4_a_ upper end surface
5 pivot member
7 liquid reservoir
22_b_ second accommodation portion (accommodation portion)
22_f_ restriction portion
53 cover portion
54 holding portion
62 vibrating plate
B battery

The invention claimed is:

1. An atomizer comprising:
a device body;
a liquid reservoir provided within the device body and configured to reserve a liquid therein;
a wick that is to be sunk at its lower end portion in a liquid reserved within the liquid reservoir;
a vibrating plate having a large number of pores and being configured to come into face contact with an upper end surface of the wick, the atomizer being configured to atomize through the pores of the vibrating plate a liquid absorbed up to the upper end surface of the wick, by vibrating the vibrating plate while keeping the vibrating plate in face contact with the upper end surface of the wick; wherein the atomizer further comprises a pivot member mounted on an upper portion of the device body so as to pivot up and down, the pivot member has a holding portion to hold the vibrating plate movable up and down relative to the pivot member so as to bring the vibrating plate into face contact with the upper end surface of the wick by the own weight of the vibrating plate when the pivot member pivots downward, and the device body has a restriction portion that comes into contact with the pivot member to restrict the pivoting downward of the pivot member while the vibrating plate is in face contact with the upper end surface of the wick.

2. The atomizer according to claim 1, wherein the device body has a recessed accommodation portion capable of accommodating a battery that is a driving source to vibrate the vibrating plate, and the pivot member has a cover portion to overlie at least a part of the battery accommodated in the accommodation portion when the pivot member pivots downward.

* * * * *